(12) United States Patent  
Hartley et al.

(10) Patent No.: US 8,864,819 B2
(45) Date of Patent: Oct. 21, 2014

(54) STENTED SIDE BRANCH GRAFT

(75) Inventors: David Ernest Hartley, Subiaco (AU); Susan Morriss, Freemantle (AU)

(73) Assignee: Cook Medical Technologies LLC, Bloomington, IN (US)

(*) Notice: Subject to any disclaimer, the term of this patent is extended or adjusted under 35 U.S.C. 154(b) by 62 days.

(21) Appl. No.: 11/299,107

(22) Filed: Dec. 9, 2005

(65) Prior Publication Data

US 2006/0136046 A1 Jun. 22, 2006

Related U.S. Application Data

(60) Provisional application No. 60/637,334, filed on Dec. 17, 2004.

(51) Int. Cl.
*A61F 2/06* (2013.01)
*A61F 2/07* (2013.01)
*A61F 2/89* (2013.01)

(52) U.S. Cl.
CPC ... *A61F 2/07* (2013.01); *A61F 2/89* (2013.01); *A61F 2002/075* (2013.01); *A61F 2002/067* (2013.01)
USPC ......................................... 623/1.35; 623/1.13

(58) Field of Classification Search
USPC .............. 623/1.13, 1.35, 1.11, 1.37, 1.16
See application file for complete search history.

(56) References Cited

U.S. PATENT DOCUMENTS

| | | | |
|---|---|---|---|
| 4,502,159 A | 3/1985 | Woodroof et al. | |
| 4,994,071 A * | 2/1991 | MacGregor | 606/194 |
| 5,676,697 A * | 10/1997 | McDonald | 623/1.35 |
| 5,711,969 A | 1/1998 | Patel et al. | |
| 5,885,619 A | 3/1999 | Patel et al. | |
| 5,955,110 A | 9/1999 | Patel et al. | |
| 5,968,096 A | 10/1999 | Whitson et al. | |
| 6,056,775 A * | 5/2000 | Borghi et al. | 623/1.16 |
| 6,086,611 A * | 7/2000 | Duffy et al. | 623/1.35 |
| 6,099,560 A * | 8/2000 | Penn et al. | 623/1.35 |
| 6,206,931 B1 | 3/2001 | Cook et al. | |
| 6,358,284 B1 | 3/2002 | Fearnot et al. | |
| 6,379,710 B1 | 4/2002 | Badylak | |
| 6,524,336 B1 * | 2/2003 | Papazolgou et al. | 623/1.35 |
| 6,576,009 B2 * | 6/2003 | Ryan et al. | 623/1.35 |
| 6,645,242 B1 * | 11/2003 | Quinn | 623/1.16 |

(Continued)

FOREIGN PATENT DOCUMENTS

| | | |
|---|---|---|
| EP | 0 904 745 | 3/1999 |
| WO | WO 98/53761 | 12/1998 |
| WO | WO 2005/034808 | 4/2005 |
| WO | PCT/US2005/044595 | 4/2006 |

*Primary Examiner* — Kathleen Holwerda
*Assistant Examiner* — Sarah Simpson
(74) *Attorney, Agent, or Firm* — Brinks Gilson & Lione

(57) ABSTRACT

A stent graft (1) has a tubular body (3) defining a main lumen and a side tube (5) defining a side tube lumen and in fluid communication with the main lumen and defining a junction (13) between the tubular body and the side tube. The junction includes an acute angle of attachment ($\alpha$). A first zig-zag stent (15) is wrapped around the tubular body such that a V portion of the first zig-zag stent is engaged about the acute angle of the junction and a second zig-zag stent (23) is wrapped around the side tube, such that a V portion of the second zig-zag stent is engaged about the acute angle of the junction, whereby the main lumen and the side tube are each kept open, independently, allowing fluid to flow freely therethrough.

12 Claims, 3 Drawing Sheets

(56) References Cited

U.S. PATENT DOCUMENTS

| | | |
|---|---|---|
| 6,666,892 B2 | 12/2003 | Hiles et al. |
| 6,673,107 B1 * | 1/2004 | Brandt et al. .................. 623/1.35 |
| 6,749,628 B1 * | 6/2004 | Callol et al. .................. 623/1.15 |
| 6,811,566 B1 * | 11/2004 | Penn et al. .................... 623/1.15 |
| 7,118,593 B2 * | 10/2006 | Davidson et al. ............. 623/1.15 |
| 7,122,052 B2 * | 10/2006 | Greenhalgh .................. 623/1.35 |
| 2001/0037138 A1 * | 11/2001 | Wilson et al. ................. 623/1.11 |
| 2002/0052644 A1 * | 5/2002 | Shaolian et al. .............. 623/1.13 |
| 2002/0065552 A1 | 5/2002 | Jayaraman et al. |
| 2002/0072790 A1 * | 6/2002 | McGuckin et al. ........... 623/1.12 |
| 2003/0097169 A1 * | 5/2003 | Brucker et al. ............... 623/1.11 |
| 2003/0199967 A1 * | 10/2003 | Hartley et al. ................ 623/1.13 |
| 2004/0098114 A1 * | 5/2004 | Wilson et al. ................. 623/1.35 |
| 2004/0117003 A1 * | 6/2004 | Ouriel et al. .................. 623/1.35 |
| 2004/0186560 A1 * | 9/2004 | Alt ................................ 623/1.35 |
| 2004/0193254 A1 * | 9/2004 | Greenberg et al. ........... 623/1.35 |
| 2005/0228484 A1 * | 10/2005 | Stephens et al. .............. 623/1.16 |
| 2005/0234542 A1 * | 10/2005 | Melsheimer .................. 623/1.35 |
| 2006/0079956 A1 * | 4/2006 | Eigler et al. .................. 623/1.35 |
| 2007/0010874 A1 * | 1/2007 | Sun ............................... 623/1.35 |

* cited by examiner

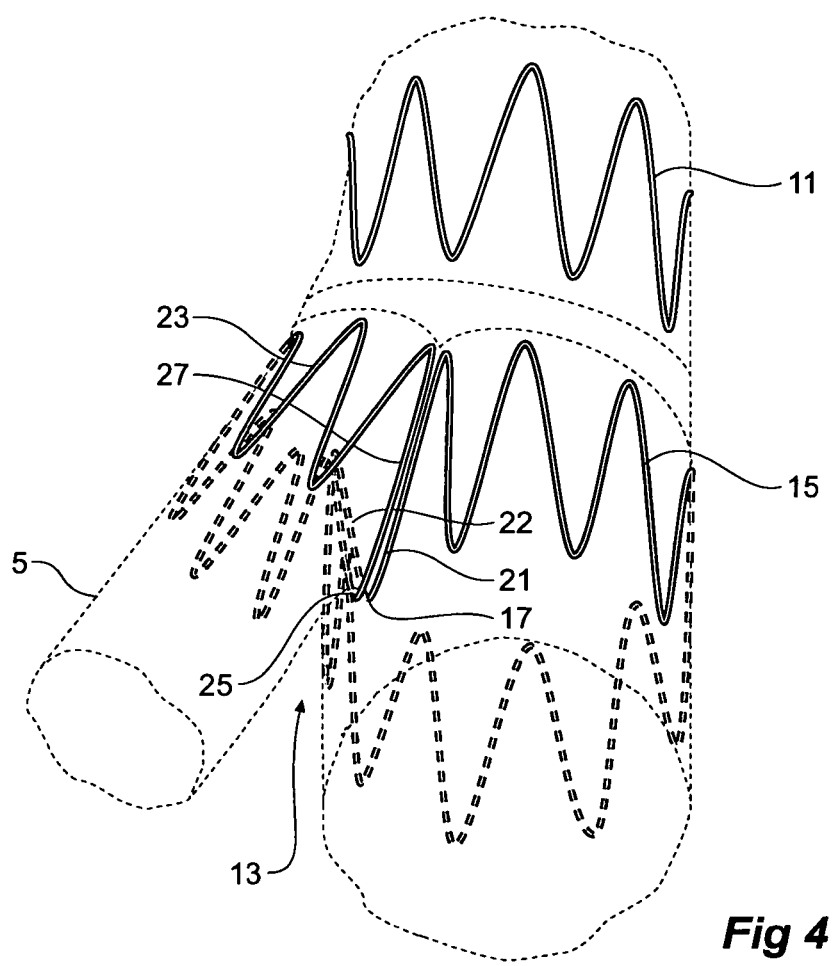

STENTED SIDE BRANCH GRAFT

CROSS-REFERENCE TO RELATED APPLICATIONS

This application claims priority of provisional application Ser. No. 60/637,334, filed Dec. 17, 2004.

TECHNICAL FIELD

This invention relates to a stent graft used to restore the patency of a body lumen and in particular relates to a side branch or side arm stent graft.

BACKGROUND OF THE INVENTION

Where damage has occurred to an internal vessel of the human or animal body such as a blood vessel either by disease or by trauma it is possible to introduce a stent graft to the blood vessel by endoluminal techniques which will restore patency of the blood vessel across the damaged region. Often such damaged regions include side branch vessels. To ensure the blood flow can go into the side branch vessel side branch stent grafts are used.

There can be a problem with such side branch stent grafts that in the region of the bifurcation or exit of a side branch from a main tube disruption to blood flow can occur. This may result in thrombosis occurring which could at least partially block the stent graft. Also, without suitable geometry, blood flowing through such regions may not adequately flow into the side arm or side branch.

It is desired to provide a branched or side arm stent graft which does not compromise blood flow in the main lumen of the stent graft and allows blood flow into the side arm.

Throughout this specification the term distal with respect to a portion of the vasculature, a deployment device or a prosthesis is the end of the vasculature, deployment device or prosthesis further away in the direction of blood flow away from the heart and the term proximal means the portion of the vasculature, deployment device or end of the prosthesis nearer to the heart. When applied to other vessels similar terms such as caudal and cranial should be understood.

SUMMARY OF THE INVENTION

In one form therefore the invention is said to reside in a stent graft comprising a tubular body defining a main lumen, at least one aperture in the tubular body of the main lumen and at least one side tube extending from the aperture defining a side tube lumen and in fluid communication with the main lumen, thereby defining a junction between the tubular body and the side tube, the junction including an acute angle of attachment, the tubular body and the side tube each including at least one self expanding zig-zag stent, each zig-zag stent comprising strut portions and bend portions, with a pair of struts and a bend between them defining a V portion, wherein a first zig-zag stent is around the tubular body such that a V portion of the first zig-zag stent is engaged about the acute angle of the junction between the main lumen and the side tube, and a second zig-zag stent is around the side tube, such that a V portion of the second zig-zag stent is engaged about the acute angle of the junction between the main lumen and the side tube, whereby the main lumen and the side tube are each kept open, independently, allowing fluid to flow freely therethrough.

In an alternative form the invention provides a stent graft comprising a tubular body defining a main lumen, at least one side tube extending from the tubular body defining a side tube lumen and in fluid communication with the main lumen, thereby defining a junction between the tubular body and the side tube, the junction including an acute angle of attachment, the stent graft further comprising a plurality of self expanding zig-zag stents, each zig-zag stent comprising strut portions and bend portions, with a pair of struts and a bend between them defining a V portion, wherein a first zig-zag stent is around the tubular body such that a V portion of the first zig-zag stent is engaged about the acute angle of attachment of the junction between the main lumen and the side tube, and a second zig-zag stent is around the side tube, such that a V portion of the second zig-zag stent is engaged about the acute angle of the junction between the main lumen and the side tube, whereby the main lumen and the side tube are each independently kept open, allowing fluid to flow freely therethrough.

In an further alternative form the invention provides a stent graft including main tube and a side tube with an acute angled bifurcation therebetween and zig-zag stents fitted onto both the main tube and the side tube at the bifurcation with the bifurcation extending down into V portions of the respective zig-zag stents.

The acute angle of attachment of the side tube to the main tube may be in the range of from 10 to 60 degrees and preferably 15 to 45 degrees.

The zig-zag stents may comprise from 8 to 16 struts with 4 to 8 each proximal and distal bends between them. The length of the zig-zag stents may range from 10 mm to 16 mm.

The zig-zag stents are preferably stitched to the outside of the tubular body and the side arm respectively.

The stents may be formed from stainless steel or nitinol.

The tubular body and the side arm may be formed from a biocompatible graft material.

The graft material is preferably non-porous so that it does not leak or sweat under physiologic forces. The graft material is preferably made of woven or knitted polyester (Vascutek Ltd., Renfrewshire, Scotland, UK). Other biocompatible fabrics, non-woven materials and porous sheets may be used as the graft material. Examples of biocompatible polymers from which porous sheets can be formed include polyesters, such as poly(ethylene terephthalate), polylactide, polyglycolide and copolymers thereof; fluorinated polymers, such as PTFE, expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any polymer that may be formed into a porous sheet can be used to make a graft material, provided the final porous material is biocompatible. Polymers that can be formed into a porous sheet include polyolefins, polyacrylonitrile, nylons, polyaramids and polysulfones, in addition to polyesters, fluorinated polymers, polysiloxanes and polyurethanes as listed above. Preferably the porous sheet is made of one or more polymers that do not require treatment or modification to be biocompatible. The graft material may include a biocompatible polyurethane. Examples of biocompatible polyurethanes include THORALON® (Thoratec, Pleasanton, Calif.), BIOSPAN®, BIONATE®, ELASTHANE™, PURSIL™ and CARBO-SIL™ (Polymer Technology Group, Berkeley, Calif.). As described in U.S. Patent Application Publication No. 2002/0065552 A1, incorporated herein by reference, THORALON® is a polyetherurethane urea blended with a siloxane-containing surface modifying additive. Specifically, the polymer is a mixture of base polymer BPS-215 and an additive SMA-300. The graft material may also include extracellular matrix materials. The "extracellular matrix" is a collagen-rich substance that is found in between cells in animal tissue and serves as a structural element in tissues. It is typically a complex mixture of polysaccharides and proteins secreted by cells. The extracellular matrix can be isolated and treated in a variety of ways. Following isolation and treatment, it is referred to as an "extracellular matrix material," or ECMM. ECMMs may be isolated from submucosa (including small intestine submucosa), stomach submucosa, urinary bladder submucosa, tissue mucosa, renal capsule, dura mater, liver basement membrane, pericardium or other tissues. Purified tela submucosa, a preferred type of ECMM, has been previously described in U.S. Pat. Nos. 6,206,931, 6,358,284 and 6,666,892 as a bio-compatible, non-thrombogenic material that enhances the repair of damaged or diseased host tissues. U.S. Pat. Nos. 6,206,931, 6,358,284 and 6,666,892 are incorporated herein by reference. Purified submucosa extracted from the small intestine ("small intestine submucosa" or "SIS") is a more preferred type of ECMM for use in this invention. Anothertype of ECMM, isolated from liver basement membrane, is described in U.S. Pat. No. 6,379,710, which is incorporated herein by reference. ECMM may also be isolated from pericardium, as described in U.S. Pat. No. 4,502,159, which is also incorporated herein by reference. Irrespective of the origin of the graft material, the graft material can be made thicker by making multi-laminate constructs, for example SIS constructs as described in U.S. Pat. Nos. 5,968,096; 5,955,110; 5,885,619; and 5,711,969. All of these references are incorporated herein by reference. The stent graft according to the present invention may be used for deployment into the common iliac artery with the side arm extending towards the internal iliac so that a leg extension may be deployed through the side arm into the internal iliac artery. The leg extension may be a balloon expandable stent graft or a self expanding stent graft.

The side arm may include at its distal end, the end further away from the bifurcation, a reinforcing ring of a resilient material such as a resilient ring.

In an alternative form the invention comprises a stent graft comprising a main tube and a side tube extending from a bifurcation in the main tube and first zigzag stent fastened to and maintaining patency of the main tube at the bifurcation and a second zigzag stent fastened to and maintaining patency of the side tube at the bifurcation, the first zigzag stent and the second zigzag stent being laterally adjacent at the bifurcation.

Preferably the main tube has a diameter of from 10 to 12 mm, the side tube has a diameter of 6 to 8 mm and the side tube is joined to the main tube at the bifurcation to form an acute angle of attachment the range of from 10 to 60 degrees and preferably 15 to 45 degrees.

A stent graft according to the present invention for deployment into the common iliac artery may have the following dimensions:

Total length: 98 mm (42 mm proximal of the bifurcation and 56 mm distal of the bifurcation)
Diameter of tubular body proximal of bifurcation: 12 mm
Diameter of tubular body distal of bifurcation: 10 mm
Diameter of side arm: 8 mm
Length of side arm 14 mm
6 stents on tubular body with distal most being internal (gaps of 2 mm proximal of the bifurcation and 5 mm distal of the bifurcation between the stents)
2 stents on side arm (gap of 2 mm between stents)

BRIEF DESCRIPTION OF THE DRAWING

This then generally describes the invention but to assist with understanding reference will now be made to the accompanying drawings which show various embodiments of the invention.

In the drawings:

FIG. 4 shows schematically a portion of a stent graft incorporating the stent configuration of the present invention.

DETAILED DESCRIPTION

Figures 1, 1A:
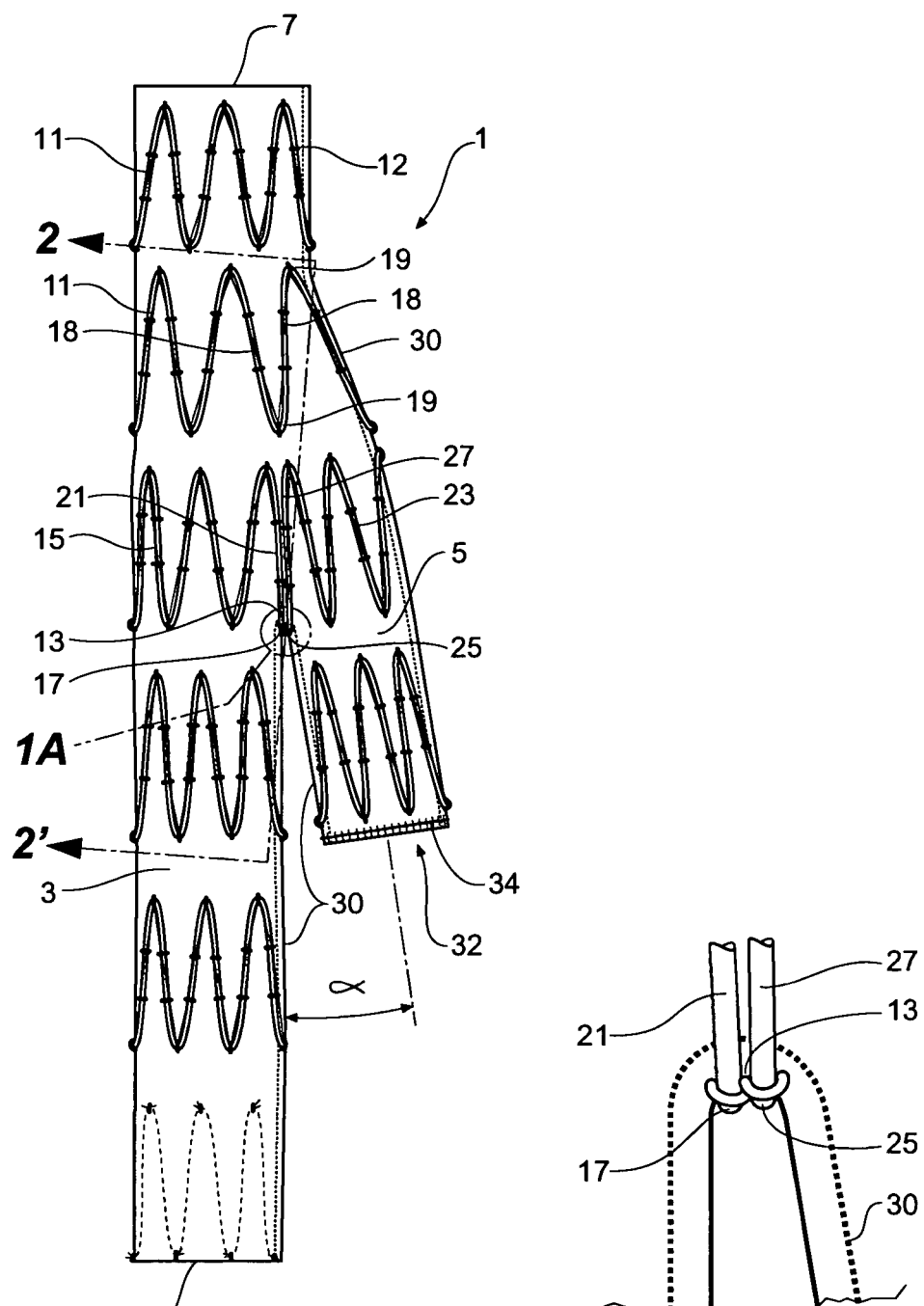
FIG. 1 shows a first embodiment of a side branch stent graft incorporating the stent configuration of the present invention.
FIG. 1A shows detail of the bifurcation area between the main tube and the side arm of FIG. 1.
Figure 2:
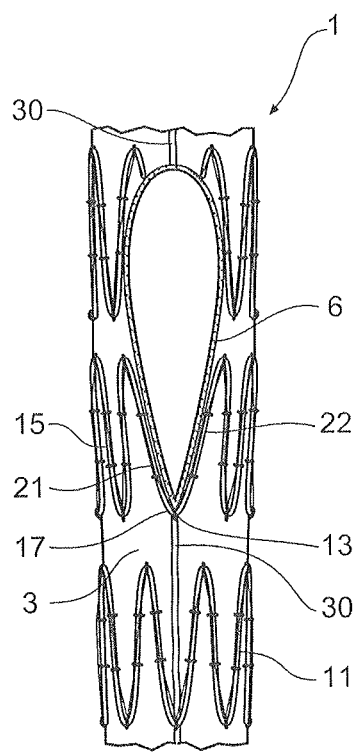
FIG. 2 shows a part section view of the side branch stent graft of FIG. 1 along the line 2-2'.

Now looking at the first embodiment shown in FIGS. 1, 1A and 2 it will be seen that a branch stent graft 1 comprises a main tube 3 and a side arm 5. The sent graft has a proximal end 7 and a distal end 9. In the deployed configuration as shown in FIG. 1 a plurality of self expanding zigzag stents 11 hold open the graft material tube to allow blood flow therethrough. Stitching 12 is used to stitch the stents 11 to the main tube 3.

Each of the stents 11 are formed with a plurality of struts 18 with bends 19 between them.

The side arm 5 is joined to the main tube at junction 6 (see FIG. 2) so that its lumen is in fluid communication with the lumen of the main tube and extends from the main tube 3 at an angle α. The angle α may be in the range of 10 to 60° and in this embodiment is approximately 15°. The junction of the side arm 5 to the main tube 3 defines a bifurcation 13. To maintain the patentency of both the main tube 3 and the side arm 5 at their junction the particular stent configuration of the present invention is provided. On the main tube 3 a zigzag stent 15 has one of its bends 17 abutted up to the bifurcation 13 and its struts 21 and 22 each side of the bend 17 extend up the junction between the main tube 3 and the side arm 5. The struts 21 and 22 each side of the junction are stitched to the graft material of the main tube 3.

Similarly on the side arm 5 a zigzag Z stent 23 has one of its bends 25 abutted up to the bifurcation 13 and its struts 27 either side of the bend 25 extending along the side of the junction between the main tube 3 and side arm 5. The struts 27 each side of the junction are stitched to the graft material of the side arm 5.

By this arrangement the junction between the main tube and the side arm is held open and each of the side arm and main tube are independently held open when the stent graft is in a deployed configuration.

The distal end 32 of the side arm can optionally include a resilient circumferential ring 34 stitched around the distal end to provide reinforcement and sealing when a further self expanding or balloon expandable stent is deployed through the side arm.

In FIGS. 1, 1A and 2 the graft material is formed into the main tube by joining a flat blank, which has been cut to the required shape, along one side by stitching, heat welding or the like 30.

Figure 3:
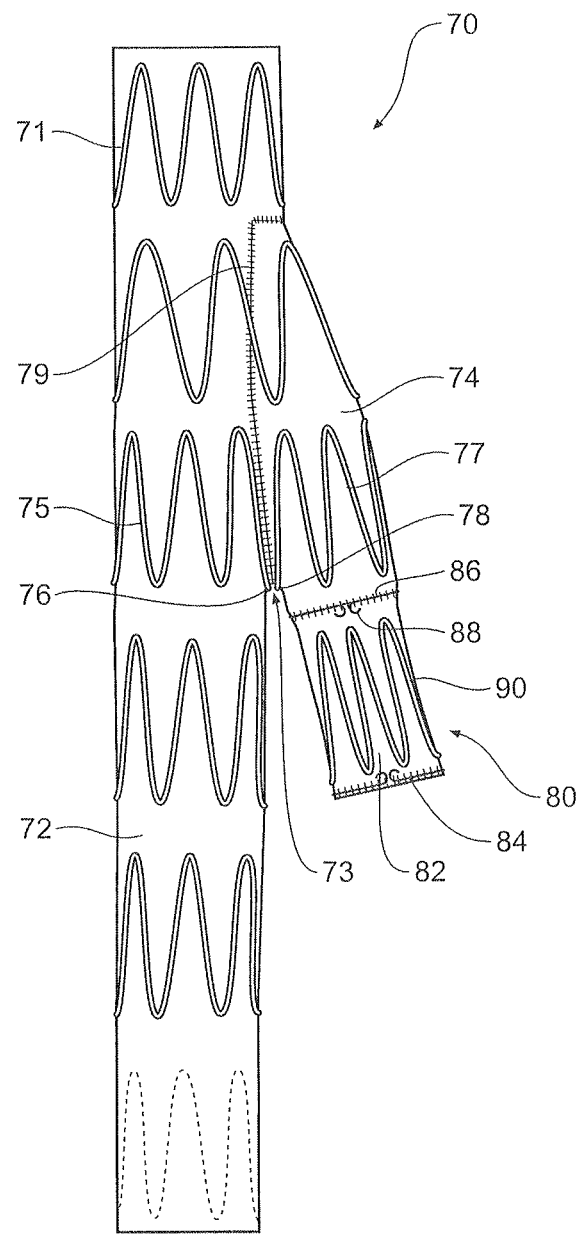
FIG. 3 shows an alternative embodiment of a side branch stent graft incorporating the stent configuration of the present invention.

FIG. 3 shows a side arm stent graft or prosthesis of the type adapted for deployment into the iliac arteries, for instance, such that a bridging stent can extend from the side arm into the internal iliac or hypogastric artery and incorporating the stent configuration of the present invention.

The stent graft 70 has a main tubular body 72 and a side arm 74 with a bifurcation 73 between them. Both the main tubular body and the side arm are formed from a seamless tube of a biocompatible graft material such as Dacron. A triangular aperture is formed in the main tube and a bevel cut into the inner end of the side arm and the side arm stitched into the triangular aperture with stitching 79.

The stent graft 70 has a plurality of self expanding Z stents 71 along the main tubular body 72. At the bifurcation 73 between the main tube 72 and the side arm 74 a self expanding Z stent 75 is placed around the main tube 72 so that a bend 76 of the stent fits against the bifurcation and its struts either side of the bend extend up the line of stitching 79 between the main tube 72 and side arm 74. Similarly at the bifurcation 73 between the main tube 72 and the side arm 74 a self expanding Z stert 77 is placed around the side arm 74 so that a bend 78 of the stent fits against the bifurcation and its struts either side of the bend extend up the line of stitching 79 between the main tube 72 and side arm 74.

The side arm 74 has a connection socket arrangement 80 at its distal end 82. The connection socket arrangement 80 comprises a first ring 84 stitched to its terminal or distal end 82 and a second ring 86 spaced apart from the first ring 84. Each ring 84 and 86 is formed from at least two turns and preferably three turns of nitinol wire and the ends of the nitinol wire terminate in loops 88. The use of the loops 88 prevent sharp ends from the nitinol wire from digging into the vasculature into which the stent graft is deployed and also provide a point to stitch the ring of wire to the graft material to prevent the ring from expanding when a balloon expanded stent in expanded within it. Between the first ring 84 and the second ring 86 is a stent 90 formed from a resilient material. The resilient stent 90 is formed from nitinol wire, for instance, and is made to be of a size which is at rest slightly smaller than the diameter of the side arm 74 and hence when sewn on to the outside of the side arm 74 it provides a diameter reducing effect on the side arm 74.

When a bridging stent such as a balloon expandable stent is placed into the socket 80 and expanded the rings 84 and 86 provide firm locking for the balloon expanded stent and the resilient stent 82 which is expanded by the balloon expanded stent while it is being balloon expanded provides a compressive effect to keep tension on the balloon expanded stent. By this means a firm connection can be obtained between the side arm and a bridging stent. A similar gripping effect can be obtained with the use of a bridging stent in the form of a self-expanding stent, a composite stent or other form of leg extension.

FIG. 4 shows detail of the bifurcation area of the side branch stent graft of the type shown in FIGS. 1 and 2. The same reference numerals are used in FIG. 4 as those in FIGS. 1 and 2 for corresponding items. The main tube 3 and side arm 5 are shown in dotted. The main body has zigzag stents 11 along its length and at the bifurcation 13 between the main tube 3 and the side arm 5 the stents 15 on the main tube and 23 on the side arm are fitted together so that their struts either side of the bifurcation extend parallel to each other such as the struts 21 on the stent graft 15 and 27 on the stent graft 23. By this arrangement the junction between the main tube and the side arm is held open and each of the side arm and main tube are independently held open when in a deployed configuration.

Throughout this specification various indications have been given has to the scope of the invention but the invention not limited one of these may reside in two or more of these combined together. The examples are given for illustration only and not for limitation.

What is claimed is:

1. A stent graft comprising a tubular body defining a main lumen, a side wall, at least one lateral aperture in the side wall of the tubular body of the main lumen and at least one side tube extending from the lateral aperture and defining an external side tube lumen in fluid communication with the main lumen, the side tube extending from the tubular body at an acute angle from the tubular tubular body, the tubular body and the side tube being formed from a biocompatible graft material, and a junction between the tubular body and the side tube, the junction defining a bifurcation between the tubular body and the side tube and having a perimeter, the tubular body and the side tube each including at least one self expanding zig-zag stent, each self expanding zig-zag stent being affixed to the graft material, each zig-zag stent comprising strut portions and bend portions, with a pair of struts and a bend between them defining a V portion, wherein a first zig-zag stent is around the tubular body such that a V portion of the first zig-zag stent is engaged about the bifurcation with adjacent strut portions extending along the sides of the junction between the tubular body and the side tube, and a second zig-zag stent is around the side tube, such that a V portion of the second zig-zag stent is engaged about the bifurcation with adjacent strut portions extending along the sides of the e junction between the tubular body and the side tube, whereby the main lumen and the side tube lumen are each kept open, independently, allowing fluid to flow freely therethrough, wherein the first and second zig-zag stents are non-concentric.

2. A stent graft as in claim 1 wherein the acute angle is in the range of from 10 to 60 degrees.

3. A stent graft as in claim 1 wherein the acute angle is in the range of from 15 to 45 degrees.

4. A stent graft as in claim 1 wherein each of the zig-zag stents comprises from 8 to 16 struts with 4 to 8 each proximal and distal bends between them.

5. A stent graft as in claim 1 wherein the length of the zig-zag stents is in the range from 10 mm to 16 mm.

6. A stent graft as in claim 1 wherein the zig-zag stents are stitched to the outside of the tubular body and the side tube respectively.

7. A stent graft as in claim 1 wherein the zig-zag stents are formed from stainless steel or nitinol.

8. A stent graft as in claim 1 wherein the graft material is selected from the group comprising woven or knitted polyester; fluorinated polymers, such as PTFE, expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments.

9. A stent graft as in claim 1 wherein the graft material comprises extracellular matrix materials.

10. A stent graft as in claim 1 wherein the side tube includes at its distal end, the end further away from the bifurcation, a reinforcing ring of a resilient material.

11. A stent graft as in claim 1 wherein the tubular body has a diameter of from 10 to 12 mm, the side tube has a diameter of 6 to 8 mm.

12. A stent graft as in claim 1 for deployment into the common iliac artery comprising the following dimensions:

Total length of 98 mm being 42 mm proximal of the bifurcation and 56 mm distal of the bifurcation;
Diameter of tubular body proximal of bifurcation 12 mm;
Diameter of tubular body distal of bifurcation 10 mm;
Diameter of side tube 8 mm;
Length of side tube 14 mm;
6 stents on tubular body with distal most being internal with gaps between the stents of 2 mm proximal of the bifurcation and 5 mm distal of the bifurcation; and
2 stents on side arm with a gap of 2 mm between stents.

* * * * *

UNITED STATES PATENT AND TRADEMARK OFFICE
CERTIFICATE OF CORRECTION

PATENT NO. : 8,864,819 B2
APPLICATION NO. : 11/299107
DATED : October 21, 2014
INVENTOR(S) : David Ernest Hartley et al.

Page 1 of 1

It is certified that error appears in the above-identified patent and that said Letters Patent is hereby corrected as shown below:

In the Claims

In column 6, claim 1, line 14, after "angle from the tubular" delete "tubular" (second occurrence).

Signed and Sealed this
Twenty-fourth Day of March, 2015

Michelle K. Lee
*Director of the United States Patent and Trademark Office*